(12) United States Patent
Fulton et al.

(10) Patent No.: US 7,527,796 B2
(45) Date of Patent: May 5, 2009

(54) GENETIC ENGINEERING OF STREPTAVIDIN-BINDING PEPTIDE TAGGED SINGLE-CHAIN VARIABLE FRAGMENT ANTIBODY TO VENEZUELAN EQUINE ENCEPHALITIS VIRUS

(75) Inventors: R. Elaine Fulton, Medicine Hat (CA); Leslie P. Nagata, Medicine Hat (CA); Azhar Z. Alvi, Mississauga (CA); Weigang Hu, Medicine Hat (CA)

(73) Assignee: Her Majesty the Queen in Right of Canada, as represented by the Minister of National Defence, Ontario (CA)

( * ) Notice: Subject to any disclaimer, the term of this patent is extended or adjusted under 35 U.S.C. 154(b) by 600 days.

(21) Appl. No.: 10/784,305

(22) Filed: Feb. 24, 2004

(65) Prior Publication Data

US 2004/0166489 A1 Aug. 26, 2004
US 2005/0118569 A1 Jun. 2, 2005

Related U.S. Application Data

(60) Provisional application No. 60/448,902, filed on Feb. 24, 2003.

(51) Int. Cl.
*A61K 39/00* (2006.01)
*A61K 39/42* (2006.01)

(52) U.S. Cl. .................................. 424/192.1; 424/159.1

(58) Field of Classification Search .............. 424/130.1, 424/135.1, 147.1, 218.1
See application file for complete search history.

(56) References Cited

OTHER PUBLICATIONS

Aubrey et al. A Recombinant scFv/Streptavidin-Binding Peptide Fusion Protein, Biol. Chem. (2001) 382:1621-1628.*
Keefe et al. One-Step Purification of Recombinant Proteins Using a Nanomolar-Affinity Streptavidin-Binding Peptide, the SBP-tag, Protein Expression and Purification (2001) 23:440-446.*

Alvi et al., "Development of a Functional Monoclonal Single-Chain Variable Fragment Antibody Against Venezuelan Equine Encephalitis Virus," Hybridoma, vol. 18, No. 5, pp. 413-421, Mary Ann Liebert, Inc. (1999).
Alvi et al., "Development of a Second Generation Monoclonal Single Chain Variable Fragment Antibody Against Venezuelan Equine Encephalitis Virus: Expression and Functional Analysis," Hybridoma and Hybridomics, vol. 21, No. 3, pp. 169-178, Mary Ann Liebert, Inc. (2002).
Alvi et al., "Functional Enhancement of a Partially Active Single-Chain Variable Fragment Antibody to Venezuelan Equine Encephalitis Virus," Viral Immunology, vol. 16, No. 2, pp. 213-222, Mary Ann Liebert, Inc. (2003).
Luo et al., "Expression of a Fusion Protein of scFv—Biotin Mimetic Peptide for Immunoassay," Journal of Biotechnology, vol. 65, pp. 225-228, Elsevier Science B.V. (1998).
George et al., "Radiometal Labeling of Recombinant Proteins by a Genetically Engineered Minimal Chelation Site: Technetium-99m Coordination by Single-Chain Fv Antibody Fusion Proteins Through a C-terminal Cysteinyl Peptide," Immunology, vol. 92, pp. 8358-8362, Proceedings of the National Academy of Science (Aug. 1995).

\* cited by examiner

*Primary Examiner*—Stacy B Chen
(74) *Attorney, Agent, or Firm*—Rader, Fishman & Grauer, PLLC

(57) ABSTRACT

A recombinant gene encoding a single-chain variable fragment (scFv) antibody against Venezuelan equine encephalitis virus (VEE) being cloned into a prokaryotic T7 RNA polymerase-regulated expression vector was disclosed. A streptavidin-binding peptide (SBP) sequence fused to a 6His tag is then attached downstream to the scFv gene. The recombinant fusion protein is expressed in bacteria and then purified by immobilized metal affinity chromatography. ELISA and Western blotting results revealed that the fusion protein not only retained VEE antigen binding and specificity properties similar to those of its parent native monoclonal antibody, but also possessed streptavidin-binding activity. This discovery obviates the need for chemical biotinylation of antibodies and the risk associated with antibody denaturation and provides a stable and reproducible reagent for rapid and efficient immunoassay of VEE.

8 Claims, 6 Drawing Sheets

```
  1 ATGGCTAAAGAAGAAGGGGTATCTCTCGAGAAAAGAGAGGCTGAAGCTGCAGGAATTCACGTGGCCCAGCCGGCCATGGCCCAGGTC
  1▸ M  A  K  E  E  G  V  S  L  E  K  R  E  A  E  A  A  G  I  H  V  A  Q  P  A  M  A  Q  V

88 CAACTGCAGGAGTCAGGACCTGAGCTGGTGAAGCCTGGGGCTTCAGTGAAGATATCCTGCAAGGCCTCTGGCTACACCTTCACTGAC
 30▸ Q  L  Q  E  S  G  P  E  L  V  K  P  G  A  S  V  K  I  S  C  K  A  S  G  Y  T  F  T  D

175 TACCATGTTCACTGGGTGAAGGGGAAGCCTGGACAGGGACTTGAATGGATTGGAAATGACTTATCCTCGATTCGATAATACTAATTAC
 59▸ Y  H  V  H  W  V  K  G  K  P  G  Q  G  L  E  W  I  G  M  T  Y  P  G  F  D  N  T  N  Y

262 AGTGAGACTTTCAAGGGCAAGGCCACATTGACTGTAGACACATCCTCCAACACAGTCTACATGCAGCTCAGCAGCCTGACATCTGAG
 88▸ S  E  T  F  K  G  K  A  T  L  T  V  D  T  S  S  N  T  V  Y  M  Q  L  S  S  L  T  S  E

349 GACACCGCTGTCTATTTTTGTGCAAGAGGTGTGGGCCTTGACTACTGGGGCCAAGGGACCACGGTCACCGTCTCCTCAGGTGGAGGC
117▸ D  T  A  V  Y  F  C  A  R  G  V  G  L  D  Y  W  G  Q  G  T  T  V  T  V  S  S  G  G  G

436 GGTTCAGGCGGAGGTGGCTCTGGCGGTGGCGGATCGGACATCGAGCTCACTCAGTCTCCAAATTCGTTGTCCACATCAATAGGAGAC
146▸ G  S  G  G  G  S  G  G  G  G  S  D  I  E  L  T  Q  S  P  N  S  L  S  T  S  I  G  D

523 AGGATCAGAATCACCTGCAAGGCCAGTCAGGATGTGGATACTGCTGTAGCCTGGTATCAACAGAGACCAGGCCAATCTCCTAAACTA
175▸ R  I  R  I  T  C  K  A  S  Q  D  V  D  T  A  V  G  W  Y  Q  Q  R  P  G  Q  S  P  K  L

610 CTGATTTTCTGGTCATCCACCCGGCACACTGGAGTCCCTGATCGCTTCACAGGCAGTGGATCTGGGACAGATTTCACTCTCACCATT
204▸ L  I  F  W  S  S  T  R  H  T  G  V  P  D  R  F  T  G  S  G  S  G  T  D  F  T  L  T  I

697 AGCAATGTGCAGTCTGAAGACTTGGCAGATTATTTCTGTCACCAATATAGCAGCTATCCATTCACGTTCGGCTCGGGGACAAAGTTG
233▸ S  N  V  Q  S  E  D  L  A  D  Y  F  C  H  Q  Y  S  S  Y  P  F  T  F  G  S  G  T  K  L

┌─ Spacer ─┐┌──── SBP ────┐┌─ Spacer ─┐
784 GAAATAAAACGGCGGCCGCCCAT TCTGGTGGTGGTGGC CATGCCATCCGCAGTTCCACGATGTTATGC GGTGGTGGCGGTTCT
262▸ E  I  K  R  A  A  A  H  S  G  G  G  G  P  C  H  P  Q  F  P  R  C  Y  A  G  G  G  G  S
          ┌── 6His ──┐
871 CATCATCATCATCATCAT TGA
291▸ H  H  H  H  H  H
```

Fig.2

GENETIC ENGINEERING OF STREPTAVIDIN-BINDING PEPTIDE TAGGED SINGLE-CHAIN VARIABLE FRAGMENT ANTIBODY TO VENEZUELAN EQUINE ENCEPHALITIS VIRUS

This Application claims the benefit of U.S. Provisional Application No. 60/448,902, filed on Feb. 24, 2003, the entire content of which is incorporated by reference in this application.

FIELD OF THE INVENTION

This invention relates to the construction of a recombinant gene encoding a single-chain variable fragment antibody cloned into an expression vector and fused with a streptavidin-binding peptide sequence to produce a fusion protein. The resultant fusion protein can be used as reagent for immunoassay of Venezuelan equine encephalitis virus when detected by horseradish peroxidase-conjugated streptavidin. This invention is related to U.S. Provisional Patent Application No. 60/361,698 filed by Fulton et al., the same inventors and assignee, which is herein incorporated by reference.

BACKGROUND OF THE INVENTION

List of Prior Art Literatures

Johnston R E and Peters C J: Alphavirus. In: *Fields virology*, 3$^{rd}$ ed. Fields B N, Knipe D M and Howley P M (Eds.), Raven Publishers, Philadelphia, Pa., 1996, pp. 843-898.

Franck P T and Johnson K M: An outbreak of Venezuelan encephalitis in man in the Panama Canal Zone. *Am J Trop Med Hyg* 1970;19:860-865.

Johnson K M, Shelokov A, Peralta P H, Dammin G J, and Young N A: Recovery of Venezuelan equine encephalomyelitis virus in Panama: a fatal case in man. *Am J Trop Med Hyg* 1968;17:432-440.

Alvi A Z, Stadnyk L L, Nagata L P, Fulton R E, Bader D E, Roehrig J T, and Suresh M R: Development of a functional monoclonal single-chain variable fragment antibody against Venezuelan equine encephalitis virus. *Hybridoma* 1999;18:413-421.

Alvi A Z, Fulton R E, Chau D, Suresh M R, and Nagata L P: Development of a second generation monoclonal single chain variable fragment antibody against Venezuelan equine encephalitis virus: expression and functional analysis. *Hybridoma and Hybridomics* 2002;21:169-178.

Alvi A Z, Hu W G, Fulton R E, Nagata L P, Coles J E, and Long M C: Functional enhancement of a partially active single chain variable fragment antibody to Venezuelan equine encephalitis virus. Viral Immunology 2003;16:213-222.

Luo D, Geng M, Schultes B, Ma J, Xu D Z, Hamza N, Qi W, Noujaim A A, and Madiyalakan R: Expression of a fusion protein of scFv-biotin mimetic peptide for immunoassay. *J. Biotechnol* 1998;65:225-228.

Long M C, Jager S, Mah D C, Jebailey L, Mah M A, Masri S A, and Nagata L P: Construction and characterization of a novel recombinant single-chain variable fragment antibody against Western equine encephalitis virus. *Hybridoma* 2000;19:1-13.

Nakamura R M: Monoclonal antibodies: methods and clinical laboratory applications. *Clin Physiol Biochem* 1983;1:160-172.

Huston J S, Levinson D, Mudgett-Hunter M, Tai M S, Novotny J, Margolies M N, Ridge R J, Bruccoleri R E, Haber E, and Crea R: Protein engineering of antibody binding sites: recovery of specific activity in an anti-digoxin single-chain Fv analogue produced in *Escherichia coli*. *Proc Natl Acad Sci USA* 1988;85:5879-5883.

Marin M, Brockly F, Noel D, Etienne-Julan M, Biard-Piechaczyk M, Hua T D, Gu Z J, and Piechaczyk M: Cloning and expression of a single-chain antibody fragment specific for a monomorphic determinant of class I molecules of the human major histocompatibility complex. *Hybridoma* 1995; 14:443-451.

Bruyns A M, De Jaeger G, De Neve M, De Wilde C, Van Montagu M, and Depicker A: Bacterial and plant-produced scFv proteins have similar antigen-binding properties. *FEBS Lett* 1996;386:5-10.

George A J, Jamar F, Tai M S, Heelan B T, Adams G P, McCartney J E, Houston L L, Weiner L M, Oppermann H, and Peters A M: Radiometal labeling of recombinant proteins by a genetically engineered minimal chelation site: technetium-99m coordination by single-chain Fv antibody fusion proteins through a C-terminal cysteinyl peptide. *Proc Natl Acad Sci USA* 1995;92:8358-8362.

Boleti E, Deonarain M P, Spooner R A, Smith A J, Epenetos A A and George A J: Construction, expression and characterisation of a single chain anti-tumour antibody (scFv)-IL-2 fusion protein. *Ann Oncol* 1995;6:945-947.

Wels W, Harwerth I M, Mueller M, Groner B, and Hynes N E: Selective inhibition of tumor cell growth by a recombinant single-chain antibody-toxin specific for the erbB-2 receptor. *Cancer Res* 1992;52: 6310-6317.

Green N M: Avidin: 1. The use of 14C-biotin for kinetic studies and for assay. *Biochem J* 1963; 89:585-590.

Guesdon J L, Ternynck T, and Avrameas S: The use of avidin-biotin interaction in immunoenzymatic techniques. *J Histochem Cytochem* 1979;27:1131-1139.

Hsu S M, Raine L, and Fanger H: Use of avidin-biotin-peroxidase complex (ABC) in immunoperoxidase techniques: a comparison between ABC and unlabeled antibody (PAP) procedures. *J Histochem Cytochem* 1981;29: 577-580.

Miralles F, Takeda Y, and Escribano M J: Comparison of carbohydrate and peptide biotinylation on the immunological activity of IgG1 murine monoclonal antibodies. *J Immunol Methods* 1991;140:191-196.

Devlin J J, Panganiban L C, and Devlin P E: Random peptide libraries: a source of specific protein binding molecules. *Science* 1990;249:404-406.

Ostergaard S, Hansen P H, Olsen M, and Holm A: Novel avidin and streptavidin binding sequences found in synthetic peptide libraries. *FEBS Lett* 1995;362:306-308.

Gissel B, Jensen M R, Gregorius K, Elsner H I, Svendsen I, and Mouritsen S: Identification of avidin and streptavidin binding motifs among peptides selected from a synthetic peptide library consisting solely of D-amino acids. *J Pept Sci* 1995; 1:217-226.

Schmidt T G, Koepke J, Frank R, and Skerra A: Molecular interaction between the strep-tag affinity peptide and its cognate target, streptavidin. *J Mol Biol* 1996; 255:753-766.

Skerra A, and Schmidt T G: Applications of a peptide ligand for streptavidin: the strep-tag. *Biomol Eng* 1999;16:79-86.

Koo K, Foegeding P M, and Swaisgood H E: Construction and expression of a bifunctional single-chain antibody against *Bacillus cereus* spores. *Appl Environ Microbiol* 1998;64:2490-2496.

Aubrey N, Devaux C, di Luccio E, Goyffon M, Rochat H, and Billiald P: A recombinant scFv/streptavidin-binding peptide fusion protein for the quantitative determination of the scorpion venom neurotoxin *Biol Chem* 2001;382:1621-1628.

Schmidt T G and Skerra A: One-step affinity purification of bacterially produced proteins by means of the "strep tag" and immobilized recombinant core streptavidin. *J Chromatogr A* 1994;676:337-345.

Zwicker N, Adelhelm K, Thiericke R, Grabley S, and Hanel F: Strep-tag II for one-step affinity purification of active bHLHzip domain of humanc-myc. *Biotechniques* 1999; 27:368-375.

Sutton M R, Fall R R, Nervi A M, and Alberts A W, Vagelos P R, and Bradshaw R A: Amino acid sequence of *Escherichia coli* biotin carboxyl carrier protein (9100). *J Biol Chem* 1977;252:3934-3940.

Venezuelan equine encephalitis virus (VEE), belonging to alphavirus genus of the family Togaviridae, is an important pathogen of epidemics in humans and of epizootics in some animals (Johnston et al., 1996). VEE causes a spectrum of human diseases ranging from inapparent infection to acute encephalitis (Franck et al; 1970; Johnson et al., 1968). Since the VEE genome is composed of positive sense RNA, its nucleic acid is infectious independent of the complete viral particle (Johnston et al., 1996). Furthermore, VEE is highly infectious by aerosol inhalation in humans (Johnston et al., 1996). Thus, VEE is a potential biological warfare and bioterrorist agent of concern. Therefore, simple, stable, and efficient immunoassays are required for rapid identification of VEE in environmental or clinical samples in order that immediate therapeutic and preventive counter measures can be taken to limit the epidemic spread of VEE infection.

The present inventors have previously cloned and characterized several single-chain variable fragment antibodies (scFv Abs) against VEE (Alvi et al., 1999; Alvi et al., 2002; Alvi et al., 2003). Among them, mA116 scFv Ab was well characterized, showing sensitivity and specificity in recognition of VEE by immunoassay (Alvi et al., 2003). In order to further explore the potentiality of mA116 scFv Ab as an immunodiagnostic reagent for detecting VEE, the present inventors successfully fused a streptavidin-binding peptide (SBP) to mA116 scFv Ab by DNA recombinant technique. This confers a streptavidin-binding function on the mA116 scFv Ab and therefore obviates the need for conventional chemical biotinylation. Chemical biotinylation is commonly associated with impairment of the antigen-binding site of the Ab and it is hence desirable to use the recombinant SBP tagged mA116 scFv of the present invention as reagent to develop a simple, stable and efficient immunoassay for VEE.

SUMMARY OF THE INVENTION

It is an object of the present invention to teach a method for constructing a streptavidin-binding peptide (SBP) to the sequence for mA I16 scFv Ab to VEE. According to one aspect of the present invention, it provides a method for constructing a recombinant gene encoding a single-chain variable fragment antibody cloned into an expression vector and fused with a SBP gene sequence to produce a fusion protein, comprising: (a) encoding anti-VEE scFv Ab gene to a recombinant plasmid and inserting a SBP gene and a 6His tag downstream to develop a SBP tagged scFv Ab construct; (b) amplifying the resultant scFv/SBP/6His by polymerase chain reaction; (c) inserting the amplified PCR products into cloning vector to produce a SBP-plasmid; (d) constructing said SBP-plasmid with promoter to produce a SBP tagged scFv Ab; and (e) expressing said SBP tagged scFv Ab in *E. coli* cells as inclusion bodies and purifying the expressed SBP tagged scFv Ab by immobilized metal affinity chromatography.

It is another object of the invention to demonstrate that the recombinant fusion protein retains antigen-binding affinity to VEE and possesses streptavidin-binding function. Hence, the genetically recombinant SBP tagged mA116 scFv Ab can be used as an excellent reagent for detecting VEE by means of immunoassay. According to another aspect of the present invention, it provides a method for using the SBP tagged recombinant scFv Ab fusion protein of claim 4 for detecting VEE, comprising: (a) reacting the SBP tagged scFv Ab with a sample containing VEE for observing antigen-binding activity; and (b) analyzing the reactant by enzyme-linked immunosorbent assay (ELISA).

BRIEF DESCRIPTION OF THE DRAWINGS

FIG. 2 shows the nucleotide and deduced amino acid sequences (SEQ ID NOs. 1 and 2 respectively) of SBP tagged mA116 Ab. MA116 scFv followed by SBP and 6His tags.

FIGS. 4A & 4B show Western blotting analysis of samples from the purification of the SBP tagged mA116 scFv Ab. Samples were resolved by SDS-PAGE, transferred to Immunobilon-P membranes, and probed with: FIG. 4A: HRP-conjugated Ni-NTA. FIG. 4B: HRP-conjugated streptavidin. Lane 1—bacterial lysate; Lane 2—solubilized protein fraction; Lane 3—column flow through fraction; Lane 4—purified fraction.

FIG. 5A: Various concentrations of Abs were added to 96-well plate coated with 10 μg/ml of VEE; FIG. 5B: 10 μg/ml of Abs were added to a 96-well plate coated with various concentrations of VEE. Binding was detected with HRP-conjugated streptavidin or HRP-conjugated anti-mouse Ig followed by ABTS solution. Each point represents the mean ± the standard error of the mean (SEM) of the four determinations.

DETAILED DESCRIPTION OF THE INVENTION

Materials and Methods

Construction of pCRT7mA116SBP

Figure 1:
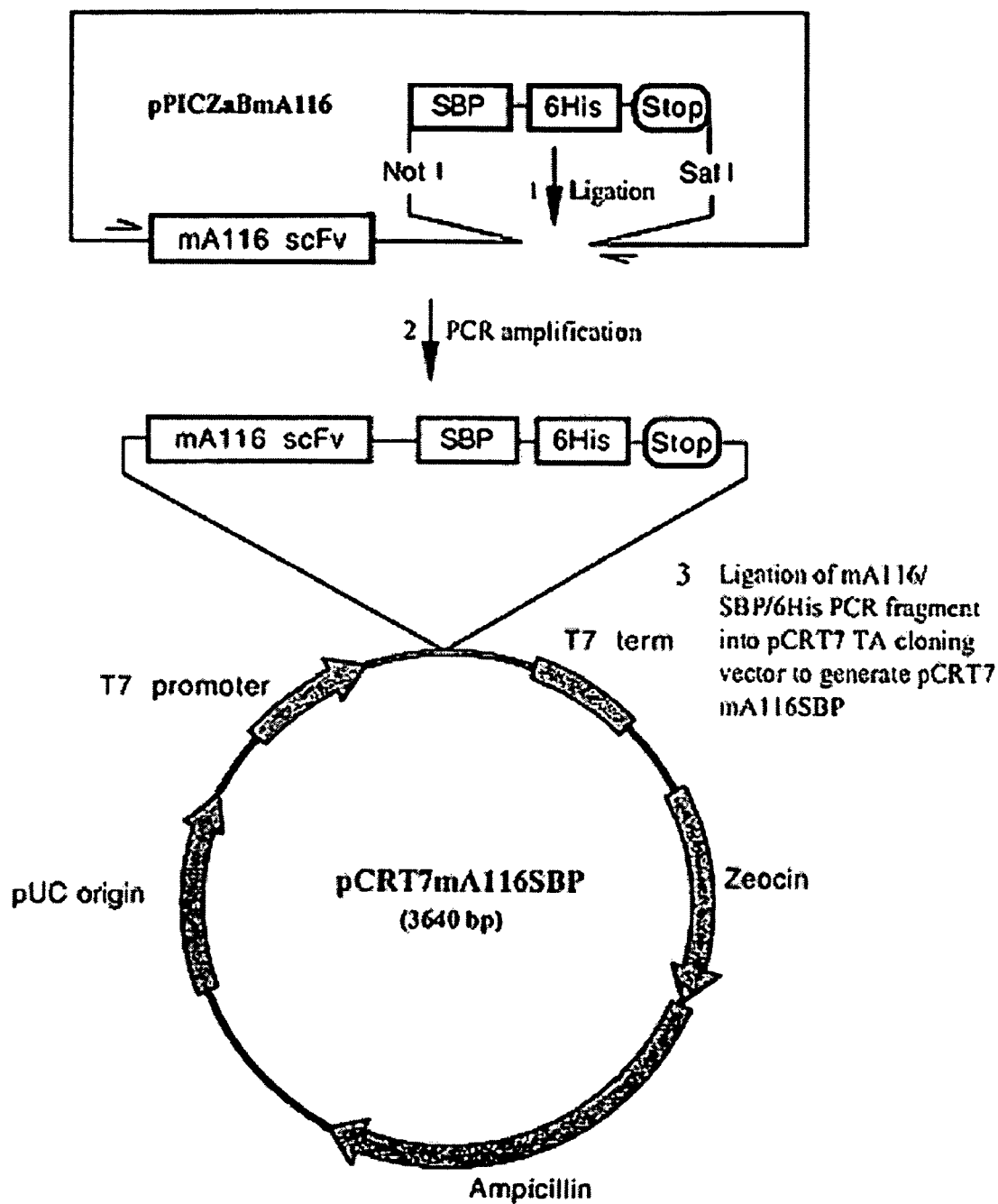
FIG. 1 is a schematic diagram showing the construction of pCRT7mA116SBP. Step 1—A single double-stranded oligonucleotide encoding SBP and 6His flanked by Not I and Sal I sticky ends was ligated into pPICZαBmA116 digested with NotI/Sal I. Step 2—scFv/SBP/6His tag sequence was amplified from pPICZαBmA116SBP vector by PCR. Step 3—PCR product was ligated into pCRT7 TA cloning vector as described under "Materials and Methods".

The pPICZαBmA116 recombinant plasmid, containing anti-VEE mA116 scFv Ab gene, arranged in variable heavy (VH)-variable light (VL) chain orientation via $(Gly_4Ser)_3$ linker, was constructed previously. In order to introduce a SBP sequence, PCHPQFPRCYA (SEQ ID NO. 3) (Lue et at., 1998) followed by a 6His tag at the C-terminus of mA116 scFv Ab, two complementary oligonucleotides corresponding to the SBP sequence and 6His tag with flanking sequences for restriction enzymes Not I and Sal I, were synthesized and purified by Life Technologies (Burlington, ON). The sequences were as follows: sense, 5'-ggccgcCCATTCTG-GTGGTGGTGGCCCATGCCATCCGC AGTTCCCAC-GATGTTATGCGGGTGGTGGCGGTTCT-CATCATCATCATCATCAT TGAg-3' (SEQ ID NO. 4); anti-sense, tcgacTCAATGATGATGATGATGATGAGAAC CGCCACCACCCGCATAACATCGTGG-GAACTGCGGATGGCATGGGCCACCACC ACCA-GAATGGgc-3' (SEQ ID NO. 5). The two oligonucleotides were heated to denature, and then annealed to a single double-stranded oligonucleotide by slow cooling to room temperature. The annealed dimer possessed a Not I sticky end on one side and Sal I on the other side, and was ligated to pPIC-ZαBmA116 that had been cut with Not I and Sal I. The resulting plasmid was named pPICZαBmA116SBP.

To obtain high expression of the recombinant fusion protein, the PCR method was introduced to amplify the mA116 scFv/SBP/6His sequence in pPICZαBmA116SBP vector and the PCR product was subcloned into a T7 RNA polymerase-regulated expression vector. Two primers were synthesized on an Oligo 1000 DNA synthesizer (Beckman Instruments, Fullerton, Calif.). The sequence of the forward primer was 5'-ATGGCTAAAGAAGAAGGGGTATC-3' (SEQ ID NO. 6) and the reverse was 5'-TCATGTCTAAGGCTACAAACT-CAA-3' (SEQ ID NO. 7). PCR reaction in a 50 µl volume consisted typically of 200 µmol each dNTP, 0.6 µM primers, 0.1 µg template, and 1.25 unit of HotStarTaq™ DNA polymerase in buffer supplied by the manufacturer (Qiagen, Mississauga, ON). Initial activation (95° C. for 15 min) was carried out followed by cycling (94° C. for 1 min, 61° C. for 1 min, and 72° C. for 2 min), repeated 30 times, on a Peltier Thermal Cycler (DNA Engine PTC-200; MJ Research, Watertown, Mass.). After gel-purification, the PCR fragment was cloned into the pCRT7 vector by use of a pCRT7 TA cloning expression kit in accordance with the manufacturer's instructions (Invitrogen, Carlsbad, Calif.). The recombinant plasmid, named pCRT7mA116SBP, contained the correct orientation of the insert, mA116 scFv/SBP/6His tag, as confirmed by restriction digestion fragment mapping and DNA sequencing.

Expression, Purification and Refolding of the SBP Tagged mA116 scFv Ab

Expression, purification and refolding of the SBP tagged mA116 scFv Ab were performed using minor modifications of previously described methodologies (Long et al., 2000). In brief, an overnight culture of E. coli BL-21 (DE3) pLys cells that had been transformed with pCRT7mA116SBP vector, was diluted 1:50 with LB-medium containing 100 µg/ml ampicillin and incubated with shaking at 37° C. to $OD_{600}$ of 0.5. The promoter was then induced for 3 hr by isopropyl β-D-thiogalactoside (IPTG). The cell pellet was resuspended in 5 mM borate sodium, pH 9.3 and 4 M urea, and cell lysate was prepared by sonication (three cycles of 10 sec; amplitude 10 µm; 15 sec cooling on ice), using a MSE Soniprep 150-probe sonicator (Wolf Laboratories, Pocklington, UK). The sonicates were centrifuged (13,000 g for 10 min) and pellets were resuspended in 5 mM borate sodium, pH 9.3, 8 mM urea, and 100 mM sodium chloride (solubilizing agent). Purification of the recombinant protein was performed on Talon™ metal affinity resin (Clontech, Palo Alto, Calif.). A solution of 5 mM borate sodium, pH 9.3, 8 M urea, and 100 mM sodium chloride was used as wash buffer. Bound fractions were eluted with 100 mM imidazole and then 1 M arginine (final concentration) was added as cosolvent, to encourage the correct folding of the protein molecules. The recombinant protein was refolded by removal of 8 M urea, by dialyzing against 5 mM borate sodium, pH 9.3, and 1 M arginine; the cosolvent was then removed by dialyzing against 5 mM borate sodium, pH 9.3. The purity was checked by sodium dodecyl sulfate-polyacrylamide gel electrophoresis (SDS-PAGE) and Coomassie brilliant blue R-250 (Bio-Rad Laboratories, Mississauga, ON) staining after samples had been concentrated in dialysis bags on a bed of polyethylene glycol compound, molecular weight (MW) 15,000-20,000 (Sigma, Oakville, ON).

SDS-PAGE and Western Blot Analysis

Proteins were separated by 10% SDS-PAGE gels by use of a Mini-PROTEAN II apparatus (Bio-Rad Laboratories). The bands were visualized by Coomassie blue staining. The molecular weights of the samples were estimated by comparison to the relative mobility values of standards of known molecular weights.

Gels were immunoblotted to Immunobilon-P membranes (Millipore Corp, Bedford, Mass.) using a western blot semi-dry transfer apparatus (Bio-Rad Laboratories) with Towbin buffer (25 mM Tris-HCl, pH 8.3, 192 mM glycine, and 20% methanol). Blots were blocked with blocking buffer (2% bovine serum albumin in phosphate-buffered saline (PBS)). Blots were washed three times for 5 min with PBS containing 0.1% tween-20 (PBST) and then incubated directly with a 1:1000 dilution of HRP-conjugated streptavidin (Sigma) or a 1:2000 dilution of HRP-conjugated Ni-nitrilotriacetic acid (NTA) (Qiagen) at room temperature for 1 hr. After three washes for 5 min with PBST, and two washes for 2 min with deionized water, the specific binding was detected by an enhanced chemiluminescence kit (Amersham Pharmacia Biotech, Baie d'Urfe, QC).

Enzyme-linked Immunosorbent Assay (ELISA)

The antigen-binding activity of the purified SBP tagged mA116 scFv Ab to VEE antigen was determined by an ELISA. Nunc maxisorp™ flat-bottomed 96-well plates (Life Technologies) were coated overnight at 4° C. with whole VEE (strain TC-83) at a fixed concentration of 10 µg/ml, or various concentrations of 0.2-60 µg/ml, in carbonate bicarbonate buffer, pH 9.6, containing 0.02% sodium azide. The plates were washed five times with PBST and then blocked twice in 2% bovine serum albumin for 1 hr at 37° C. After five washes with PBST, plates were incubated for 1 hr at 37° C. with various concentrations of 0.6-50 µg/ml, or a fixed concentration of 10 µg/ml of the SBP tagged mA116 scFv Ab or its parental monoclonal antibody (MAb) 1A4A1, diluted in PBST. Following five washes with PBST, plates were incubated for 1 hr at 37° C. with 1:1000 dilution of HRP-conjugated streptavidin in PBST for the SBP tagged mA116 scFv Ab and 1:2000 dilution of HRP-conjugated goat anti-mouse Ig for 1A4A1 MAb. Finally, the plates were washed five times with PBST and developed for 30 min at room temperature with a substrate consisting of 2,2'-azino-di-(3-ethyl-benzthiazoline-sulfonic acid) diammonium salt (ABTS) and hydrogen peroxidate (Kirkegaard and Perry Laboratories, Gathersburg, Md.). The reactions were read at an absorbance of 405 nm by a microplate autoreader (Molecular Devices, Sunnyvale, Calif.).

Results

Construction, Expression and Purification

The pPICZαBmA116 recombinant plasmid, encoding anti-VEE mA116 scFv Ab gene was used as a source material to create the SBP tagged mA116 scFv Ab construct. After a synthetic double-stranded oligonucleotide encoding a SBP and 6His tag was inserted downstream to the pPICZ- αBmA116, mA116 scFv/SBP/6His was amplified using PCR method with appropriate primers. The PCR product was inserted into pCRT7 TA cloning vector. The resulting plasmid, designated pCRT7mA116SBP, contained the mA116 scFv Ab gene, followed by the SBP sequence under the control of T7 promoter (FIG. 1). In addition, there was a 6His tag located downstream of the SBP for immobilized metal affinity chromatography (IMAC) purification. The nucleotide and deduced amino acid sequences are showed in FIG. 2. The encoded whole recombinant fusion protein was 296 residues with a predicted molecular weight of 31.3 kDa.

Figure 3:
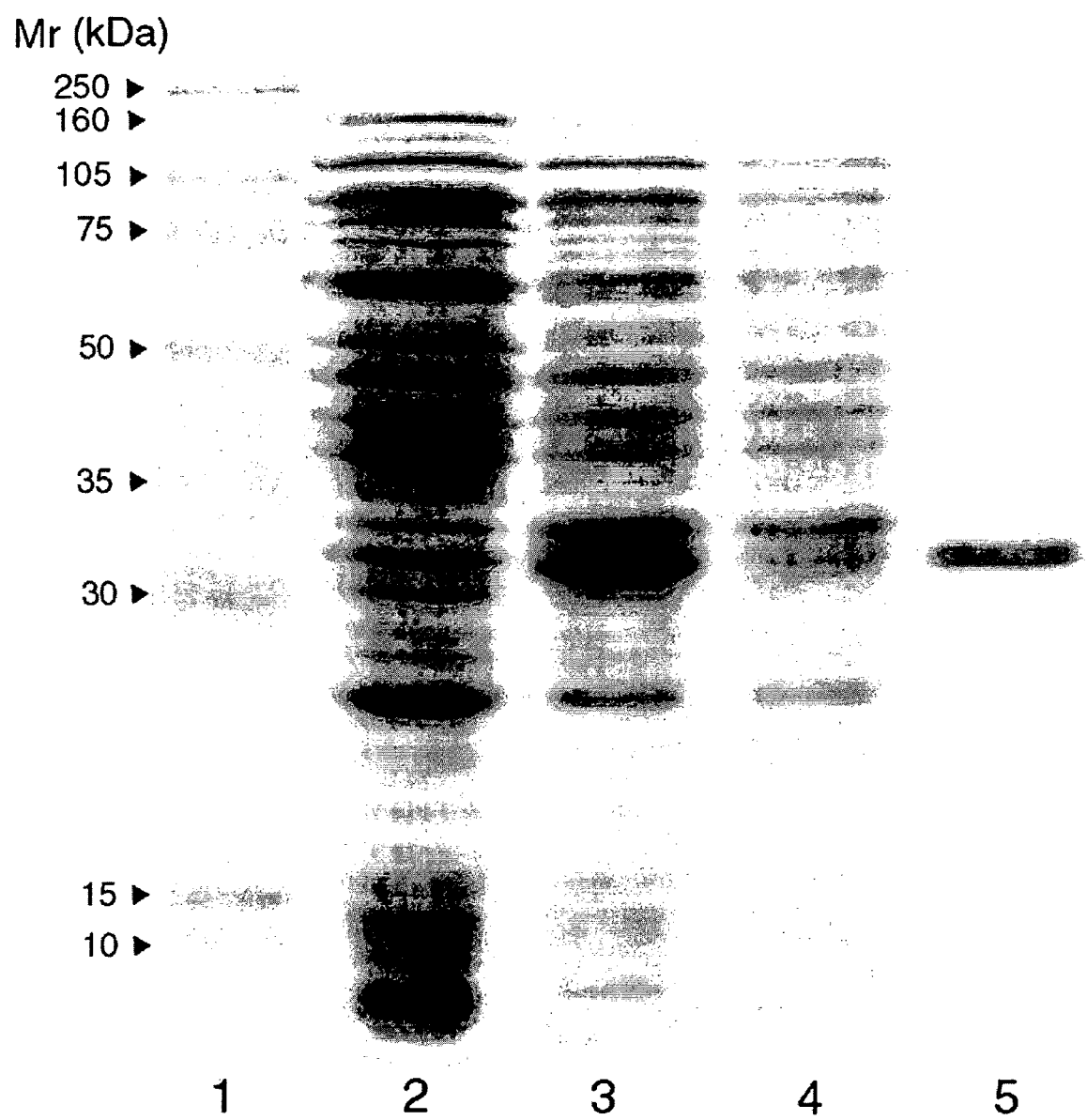
FIG. 3 shows SDS-PAGE analysis of samples from the purification of the SBP tagged mA116 scFv Ab. Samples were resolved on 10% polyacrylamide gel and stained with Coomassie blue. Lane 1—molecular weight markers; Lane 2—bacterial lysate; Lane 3—solubilized protein fraction; Lane 4—column flow through fraction; Lane 5—purified fraction.

The SBP tagged mA116 scFv Ab was expressed in *E.coli* BL-21 cells as inclusion bodies and purified by IMAC. SDS-PAGE demonstrated that there was a relatively small amount of protein in the bacterial lysate of molecular weight ~32 kDa corresponding to the predicted size (31.3 kDa) of the SBP tagged mA116 scFv Ab, due to the presence of large amounts of contaminating proteins (FIG. 3, Lane 2). However, after centrifugation of the lysate, and dissolution of the pellet in solubilizing agent, many of the bacterial host proteins were removed from the lysate, making the ~32 kDa band more visible (FIG. 3, Lane 3). The solubilized protein fraction was incubated with metal affinity resin and loaded to an empty column. After thoroughly washing with wash buffer, the bound fractions were eluted by 100 mM imidazole. Only one band of ~32 kDa was observed in the purified fraction (FIG. 3, lane 5). In this purification protocol, the expressed protein could be purified to over 90%.

Biochemical Characterization

Figure 4:
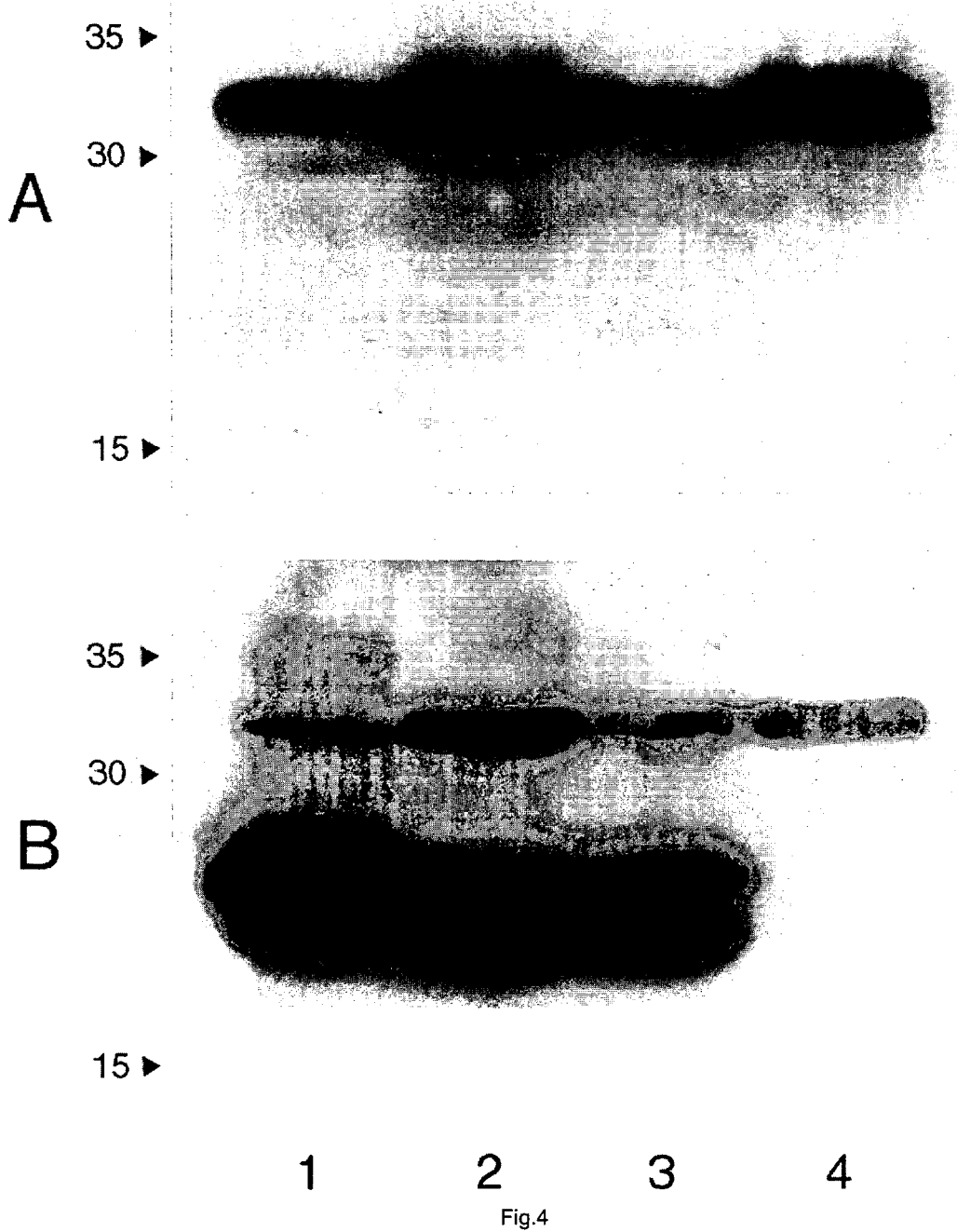

To confirm the integrity of the expressed SBP tagged mA116 scFv Ab, a series of Western blotting experiments was performed, in which the 32-kDa protein was detected by both HRP-conjugated streptavidin and HRP-conjugated Ni-NTA (FIG. 4). With HRP-conjugated Ni-NTA, a 32 kDa band was observed in all purification fractions (FIG. 4A, Lanes 2-4). With HRP-conjugated streptavidin, bands were visible at 32 kDa in all fractions (FIG. 4B, Lanes 2-4). In addition, bands were observed at 20 kDa in the bacterial lysate, solubilized protein fraction, and column flow through fraction (FIG. 4B, Lanes 1-3). However, after purification, only the 32 kDa band was present in the purified fraction (FIG. 4B, Lane 4).

Binding Properties to VEE Antigen

Figure 5A:
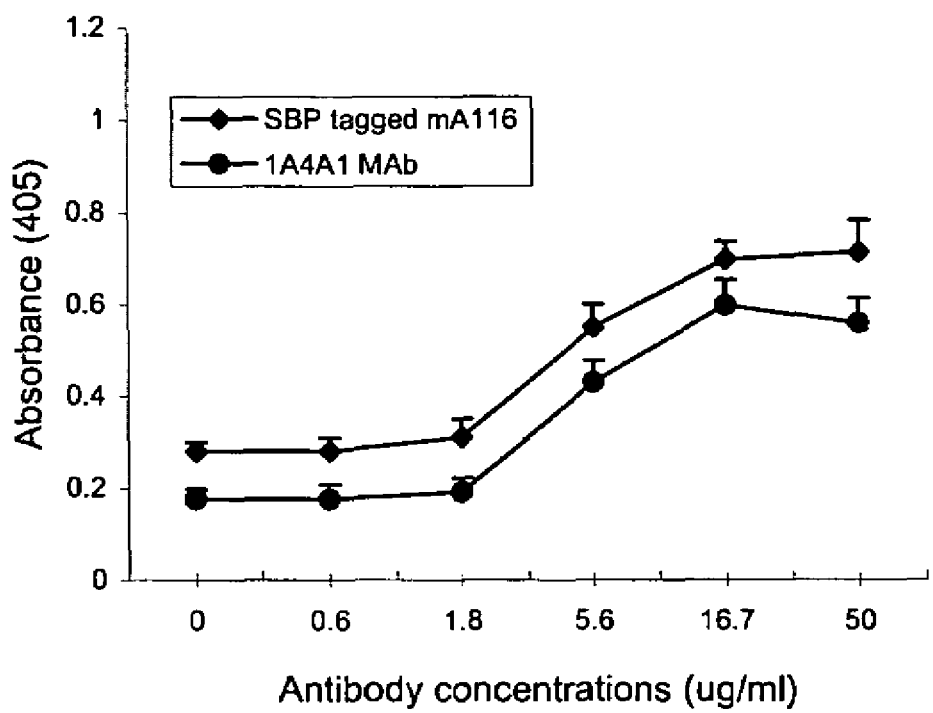
FIGS. 5A & 5B are graphs showing VEE antigen binding assay by ELISA.
Figure 5B:
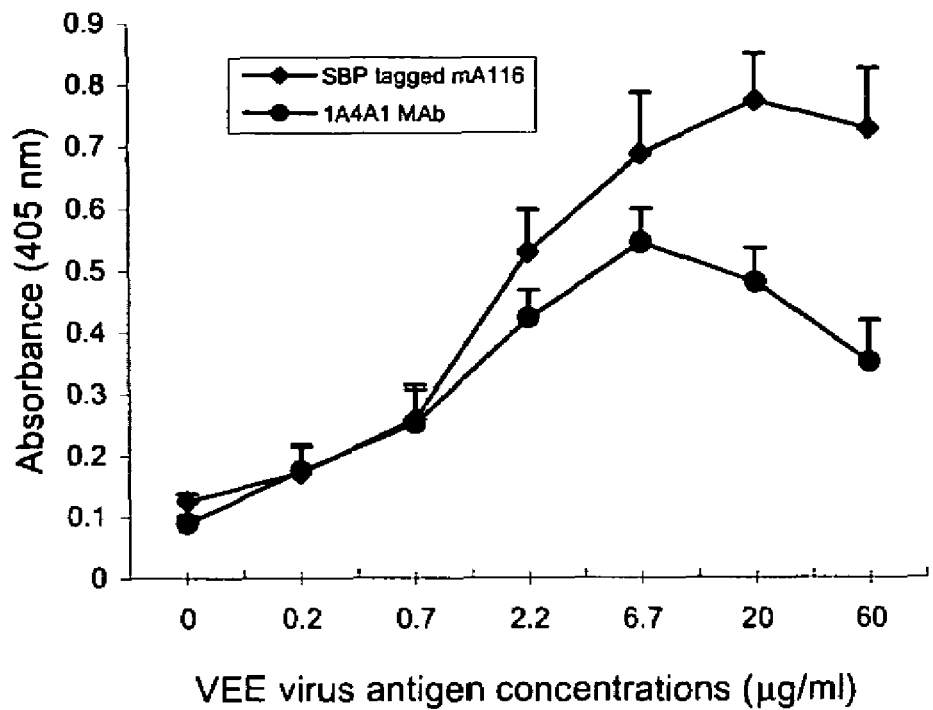

The immunoreactivity of the SBP tagged mA116 scFv Ab to VEE antigen was examined by ELISA. When the plates were coated with a fixed concentration of VEE (10 µg/ml), the SBP tagged mA116 scFv Ab bound to VEE in a dose-dependent manner, similar to the binding to VEE of its parental 1A4A1 MAb (FIG. 5A). An additional ELISA was performed in which a concentration gradient of VEE was titrated against a fixed concentration of Abs (10 µg/ml). A similar dose-response relationship was observed (FIG. 5B).

Discussion

Since the introduction of MAb technology, a number of types of immunodiagnostic assays have been developed based on specific binding between antigens and their corresponding MAbs (Nakamura, 1983). However, the disadvantages of MAbs as immunodiagnostic reagents are numerous. The cost and time required for growth and maintenance of hybridoma cell lines, and production and purification of MAbs, coupled with the potential for occurrence of genetic mutation during repeated cycles of cell growth, makes routine production of MAbs from hybridoma cell lines difficult, expensive, and time consuming. ScFv Abs are comprised of immunoglobulin VH and VL chains, covalently connected by a peptide linker (Huston et al., 1988). These small proteins generally retain the specificity and affinity for antigen similar to their parental MAb and possibly bind to poorly accessible epitopes more efficiently due to their small size (Marin et al., 1995; Bruyns et al., 1996). The attractiveness of scFv Abs is that they can be produced economically in bacteria and manipulated via genetic engineering, for example to form fusion proteins with additional functions (George et al., 1995; Boleti et al., 1995; Wels et al., 1992).

The streptavidin-biotin system has one of the highest affinities ($10^{-15}$ M) among receptor-ligand interactions (Green, 1963). The strong interaction between streptavidin and biotin has been applied in many immunoassays (Guesdon et al., 1979; Hsu et al., 1981). However, chemical biotinylation of Ab is time-consuming and, as most of the biotin binds to amino groups of the protein, the degree of labeling can differ from batch to batch. Furthermore, the possibility exists that the biological activity of the Ab may be affected by the labeling procedure (Mirables et al., 1991). With advent of recombinant DNA technology, it is possible to fuse a short peptide to the target protein through gene fusion technique. SBPs, constituting around 10 amino acids have been selected from random peptide libraries (Devlin et al., 1990; Osterguard et al., 1995; Gissel et al., 1995). Some of them have been well characterized (Schmidt et al., 1996; Skewa et al., 1999). SBPs have successfully been fused to scFv Abs to antigen CA125, *Bacillus cereus* spores, and scorpion toxin for use in immunoassay (Luo et al., 1998 Kao et al., 1998 Aubrey et al., 2001).

The present inventors genetically incorporated a SBP sequence in mA116 scFv Ab gene in order to biotinylate mA116 scFv Ab. DNA sequencing confirmed that DNA cloning was successful. The SBP tagged mA I16 scFv Ab was expressed in *E. coli* to high levels in the form of insoluble inclusion bodies. The insoluble recombinant fusion protein was solubilized by denaturing agent, 8M urea. Inclusion of 6His tag allowed the solubilized recombinant fusion protein to be purified via IMAC. In this way, greater than 90% purity of the SBP tagged recombinant mA116 scFv Ab could be obtained. After purification, arginine was introduced to the recombinant protein solution to direct correct refolding.

The streptavidin-binding peptide confers reversible binding activity toward the streptavidin. Therefore, it can be employed for the one step purification of a corresponding fusion protein via streptavidin affinity chromatography (Schmidt et al., 1994; Zwicker et al., 1999). However, in the present invention, purification of the recombinant SBP tagged mA116 scFv Ab using streptavidin affinity column chromatography yielded only small amounts of product containing relatively large amounts of host proteins (data not shown). In fact, a large amount of streptavidin-binding protein of around 20 kDa showed up in the bacterial lysate on Western blot analysis of bacterial lysate (FIG. 4B). This may be attributed to whole cell extracts of *E.coli* containing biotinylated proteins, such as biotin carboxyl carrier protein (22.5 kDa) that binds strongly to streptavidin (Sutton et al., 1977). Accordingly, a 6His tag was introduced into the gene construct in order that IMAC could be used to purify the Ab of the present invention.

The results of Western blot analysis confirmed that the refolded recombinant fusion protein was intact, with a molecular weight of ~32 kDa. The in vitro binding characteristics of the SBP tagged mA116 scFv Ab to VEE antigen were assayed by ELISA. The recombinant fusion protein exhibited strong binding activity to VEE, indicating that the SBP did not interfere with the conformation of antigen-binding site or the bioactivity of mA116 scFv Ab. The parental 1A4A1 MAb showed similar binding activity to VEE. However, a direct comparison of the binding affinities between both Abs was not possible by ELISA due to the use of different HRP-conjugates.

In summary, a SBP sequence was introduced downstream to the sequence for mA116 scFv Ab to VEE. The fusion protein was expressed and purified. Fusion to the SBP did not affect the ability of mA116 scFv Ab to recognize VEE antigen with an affinity similar to that observed for the parental MAb. Similarly, the streptavidin-binding property of the fusion protein was not impaired. Western blot and ELISA results suggest that SBP tagged mA116 scFv Ab could be used for simple, stable, and efficient detection of VEE when used in conjunction with HRP-conjugated streptavidin. This approach eliminates the need for chemical biotinylation of Abs with resultant possible impairment of the antigen-binding site of the Ab.

It is to be understood that the embodiments and variations shown and described herein are merely illustrative of the principles of this invention and that various modifications may be implemented by those skilled in the art without departing from the scope and spirit of the invention.

In addition, the List of Prior Art Literatures referred to in the Background of the Invention section is incorporated by reference herein.

What is claimed is:

1. A fusion protein, SBP tagged scFv Ab, comprising a single-chain variable fragment antibody (scFvAb) fused with a streptavidin-binding peptide (SBP) sequence, said fusion protein comprising (A) the amino acid sequence encoded by the nucleotide sequence shown in SEQ ID NO: 1 or (B) the amino acid sequence shown in SEQ ID NO: 2.

2. The SBP tagged recombinant scFv Ab fusion protein of claim 1, wherein said fusion protein has a molecular weight of ~32 kDa.

3. The SBP tagged recombinant scFv Ab fusion protein of claim 1, wherein said fusion protein has an antigen-binding affinity to Venezuelan equine encephalitis virus (VEE).

4. The SBP tagged recombinant scFv Ab fusion protein of claim 1, wherein said fusion protein has streptavidin-binding activity.

5. A method for detecting VEE, comprising:
   (a) reacting the SBP tagged recombinant scFv Ab fusion protein of claim 4 with a sample containing VEE for observing antigen-binding activity; and
   (b) analyzing the reactant by enzyme-linked immunosorbent assay (ELISA).

6. The method of claim 5, wherein said ELISA immunoassay employs an indicator enzyme and substrate system to visually indicate presence of antigen-binding activity.

7. The method of claim 6, wherein horseradish peroxidase is used in said ELISA as the indicator enzyme.

8. The method of claim 6, wherein 2,2'-azino-di-(3-ethyl-benzthiazoline-sulfonic acid) diammonium salt (ABTS) is used in said ELISA as the substrate system.

* * * * *

SEQUENCE LISTING

<160> NUMBER OF SEQ ID NOS: 7

<210> SEQ ID NO 1
<211> LENGTH: 891
<212> TYPE: DNA
<213> ORGANISM: Mouse
<220> FEATURE:
<221> NAME/KEY: CDS
<222> LOCATION: (1)..(891)
<223> OTHER INFORMATION: scFv: 1-807:
      SBP, 6His and spacers: 808-891
<300> PUBLICATION INFORMATION:
<301> AUTHORS: Wei-Gang Hu, Azhar Z. Alvi, R. Elaine Fulton,
      Mavanur R. Suresh, and Les P. Nagata
<302> TITLE: Genetic Engineering of Streptavidin-Binding Peptide Tagged
      Single-Chain Variable Fragment Antibody to Venezuelan Equine
      Encephalitis Virus
<303> JOURNAL: Hybridoma & Hybridomics
<304> VOLUME: 21
<305> ISSUE: 6
<306> PAGES: 415-420
<307> DATE: 2002

<400> SEQUENCE: 1

```
atg gct aaa gaa gaa ggg gta tct ctc gag aaa aga gag gct gaa gct        48
Met Ala Lys Glu Glu Gly Val Ser Leu Glu Lys Arg Glu Ala Glu Ala
1               5                   10                  15 gca gga att cac gtg gcc cag ccg gcc atg gcc cag gtc caa ctg cag        96
Ala Gly Ile His Val Ala Gln Pro Ala Met Ala Gln Val Gln Leu Gln
                20                  25                  30 gag tca gga cct gag ctg gtg aag cct ggg gct tca gtg aag ata tcc       144
Glu Ser Gly Pro Glu Leu Val Lys Pro Gly Ala Ser Val Lys Ile Ser
            35                  40                  45 tgc aag gcc tct ggc tac acc ttc act gac tac cat gtt cac tgg gtg       192
Cys Lys Ala Ser Gly Tyr Thr Phe Thr Asp Tyr His Val His Trp Val
        50                  55                  60 aag ggg aag cct gga cag gga ctt gaa tgg att gga atg act tat cct       240
Lys Gly Lys Pro Gly Gln Gly Leu Glu Trp Ile Gly Met Thr Tyr Pro
65                  70                  75                  80 gga ttc gat aat act aat tac agt gag act ttc aag ggc aag gcc aca       288
Gly Phe Asp Asn Thr Asn Tyr Ser Glu Thr Phe Lys Gly Lys Ala Thr
                85                  90                  95 ttg act gta gac aca tcc tcc aac aca gtc tac atg cag ctc agc agc       336
Leu Thr Val Asp Thr Ser Ser Asn Thr Val Tyr Met Gln Leu Ser Ser
                100                 105                 110 ctg aca tct gag gac acc gct gtc tat ttt tgt gca aga ggt gtg ggc       384
Leu Thr Ser Glu Asp Thr Ala Val Tyr Phe Cys Ala Arg Gly Val Gly
            115                 120                 125 ctt gac tac tgg ggc caa ggg acc acg gtc acc gtc tcc tca ggt gga       432
Leu Asp Tyr Trp Gly Gln Gly Thr Thr Val Thr Val Ser Ser Gly Gly
        130                 135                 140
```

-continued

```
ggc ggt tca ggc gga ggt ggc tct ggc ggt ggc gga tcg gac atc gag          480
Gly Gly Ser Gly Gly Gly Gly Ser Gly Gly Gly Gly Ser Asp Ile Glu
145                 150                 155                 160 ctc act cag tct cca aat tcg ttg tcc aca tca ata gga gac agg atc          528
Leu Thr Gln Ser Pro Asn Ser Leu Ser Thr Ser Ile Gly Asp Arg Ile
                165                 170                 175 aga atc acc tgc aag gcc agt cag gat gtg gat act gct gta ggc tgg          576
Arg Ile Thr Cys Lys Ala Ser Gln Asp Val Asp Thr Ala Val Gly Trp
            180                 185                 190 tat caa cag aga cca ggg caa tct cct aaa cta ctg att ttc tgg tca          624
Tyr Gln Gln Arg Pro Gly Gln Ser Pro Lys Leu Leu Ile Phe Trp Ser
        195                 200                 205 tcc acc cgg cac act gga gtc cct gat cgc ttc aca ggc agt gga tct          672
Ser Thr Arg His Thr Gly Val Pro Asp Arg Phe Thr Gly Ser Gly Ser
    210                 215                 220 ggg aca gat ttc act ctc acc att agc aat gtg cag tct gaa gac ttg          720
Gly Thr Asp Phe Thr Leu Thr Ile Ser Asn Val Gln Ser Glu Asp Leu
225                 230                 235                 240 gca gat tat ttc tgt cac caa tat agc agc tat cca ttc acg ttc ggc          768
Ala Asp Tyr Phe Cys His Gln Tyr Ser Ser Tyr Pro Phe Thr Phe Gly
                245                 250                 255 tcg ggg aca aag ttg gaa ata aaa cgg gcg gcc gca cat tct ggt ggt          816
Ser Gly Thr Lys Leu Glu Ile Lys Arg Ala Ala Ala His Ser Gly Gly
            260                 265                 270 ggt ggc cca tgc cat ccg cag ttc cca cga tgt tat gcg ggt ggt ggc          864
Gly Gly Pro Cys His Pro Gln Phe Pro Arg Cys Tyr Ala Gly Gly Gly
        275                 280                 285 ggt tct cat cat cat cat cat cat tga                                      891
Gly Ser His His His His His His
    290                 295
```

<210> SEQ ID NO 2
<211> LENGTH: 296
<212> TYPE: PRT
<213> ORGANISM: Mouse
<220> FEATURE:
<221> NAME/KEY: MISC_FEATURE
<223> OTHER INFORMATION: scFv: 1-269:
      SBP,6His and spacers: 270-296

<400> SEQUENCE: 2

```
Met Ala Lys Glu Glu Gly Val Ser Leu Glu Lys Arg Glu Ala Glu Ala
1               5                   10                  15

Ala Gly Ile His Val Ala Gln Pro Ala Met Ala Gln Val Gln Leu Gln
                20                  25                  30

Glu Ser Gly Pro Glu Leu Val Lys Pro Gly Ala Ser Val Lys Ile Ser
            35                  40                  45

Cys Lys Ala Ser Gly Tyr Thr Phe Thr Asp Tyr His Val His Trp Val
        50                  55                  60

Lys Gly Lys Pro Gly Gln Gly Leu Glu Trp Ile Gly Met Thr Tyr Pro
65                  70                  75                  80

Gly Phe Asp Asn Thr Asn Tyr Ser Glu Thr Phe Lys Gly Lys Ala Thr
                85                  90                  95

Leu Thr Val Asp Thr Ser Ser Asn Thr Val Tyr Met Gln Leu Ser Ser
            100                 105                 110

Leu Thr Ser Glu Asp Thr Ala Val Tyr Phe Cys Ala Arg Gly Val Gly
        115                 120                 125

Leu Asp Tyr Trp Gly Gln Gly Thr Thr Val Thr Val Ser Ser Gly Gly
    130                 135                 140
```

-continued

```
Gly Gly Ser Gly Gly Gly Ser Gly Gly Gly Ser Asp Ile Glu
145                 150                 155                 160

Leu Thr Gln Ser Pro Asn Ser Leu Ser Thr Ser Ile Gly Asp Arg Ile
                165                 170                 175

Arg Ile Thr Cys Lys Ala Ser Gln Asp Val Asp Thr Ala Val Gly Trp
            180                 185                 190

Tyr Gln Gln Arg Pro Gly Gln Ser Pro Lys Leu Leu Ile Phe Trp Ser
        195                 200                 205

Ser Thr Arg His Thr Gly Val Pro Asp Arg Phe Thr Gly Ser Gly Ser
    210                 215                 220

Gly Thr Asp Phe Thr Leu Thr Ile Ser Asn Val Gln Ser Glu Asp Leu
225                 230                 235                 240

Ala Asp Tyr Phe Cys His Gln Tyr Ser Ser Tyr Pro Phe Thr Phe Gly
                245                 250                 255

Ser Gly Thr Lys Leu Glu Ile Lys Arg Ala Ala Ala His Ser Gly Gly
            260                 265                 270

Gly Gly Pro Cys His Pro Gln Phe Pro Arg Cys Tyr Ala Gly Gly Gly
        275                 280                 285

Gly Ser His His His His His His
    290                 295

<210> SEQ ID NO 3
<211> LENGTH: 11
<212> TYPE: PRT
<213> ORGANISM: Artificial Sequence
<220> FEATURE:
<223> OTHER INFORMATION: Streptavidian-Binding Peptide

<400> SEQUENCE: 3

Pro Cys His Pro Gln Phe Pro Arg Cys Tyr Ala
1               5                   10

<210> SEQ ID NO 4
<211> LENGTH: 95
<212> TYPE: DNA
<213> ORGANISM: Artificial Sequence
<220> FEATURE:
<223> OTHER INFORMATION: Oligonucleotides

<400> SEQUENCE: 4
ggccgcccat tctggtggtg gtggcccatg ccatccgcag ttcccacgat gttatgcggg    60
tggtggcggt tctcatcatc atcatcatca ttgag                              95

<210> SEQ ID NO 5
<211> LENGTH: 95
<212> TYPE: DNA
<213> ORGANISM: Artificial Sequence
<220> FEATURE:
<223> OTHER INFORMATION: Oligonucleotides

<400> SEQUENCE: 5
tcgactcaat gatgatgatg atgatgagaa ccgccaccac ccgcataaca tcgtgggaac    60
tgcggatggc atgggccacc accaccagaa tgggc                              95

<210> SEQ ID NO 6
<211> LENGTH: 23
<212> TYPE: DNA
<213> ORGANISM: Artificial Sequence
<220> FEATURE:
<223> OTHER INFORMATION: DNA Primer
```

```
<400> SEQUENCE: 6
atggctaaag aagaagggt atc                                            23

<210> SEQ ID NO 7
<211> LENGTH: 24
<212> TYPE: DNA
<213> ORGANISM: Artificial Sequence
<220> FEATURE:
<223> OTHER INFORMATION: DNA Primer

<400> SEQUENCE: 7
tcatgtctaa ggctacaaac tcaa                                          24
```